(12) United States Patent
Slemker

(10) Patent No.: US 7,438,725 B2
(45) Date of Patent: Oct. 21, 2008

(54) KNEE COSMESIS

(75) Inventor: Tracy C. Slemker, Clayton, OH (US)

(73) Assignee: Prosthetic Design, Inc., Clayton, OH (US)

( * ) Notice: Subject to any disclaimer, the term of this patent is extended or adjusted under 35 U.S.C. 154(b) by 217 days.

(21) Appl. No.: 11/314,962

(22) Filed: Dec. 21, 2005

(65) Prior Publication Data

US 2007/0142924 A1 Jun. 21, 2007

(51) Int. Cl.
*A61F 2/60* (2006.01)
(52) U.S. Cl. .......................................... 623/39
(58) Field of Classification Search .............. 623/27–46
See application file for complete search history.

(56) References Cited

U.S. PATENT DOCUMENTS

| | | | | |
|---|---|---|---|---|
| 2,671,224 | A | * | 3/1954 | Regnell ........................ 623/26 |
| 3,953,900 | A | | 5/1976 | Thompson |
| 4,089,072 | A | | 5/1978 | Glabiszewski |
| 5,376,127 | A | | 12/1994 | Swanson |
| 5,458,656 | A | | 10/1995 | Phillips |
| 5,593,453 | A | | 1/1997 | Ahlert |
| 5,880,964 | A | | 3/1999 | Schall et al. |
| 6,153,139 | A | | 11/2000 | Marquette |
| 6,470,552 | B1 | | 10/2002 | Slemker et al. |
| 6,597,965 | B2 | | 7/2003 | Graves et al. |
| 6,911,049 | B2 | | 6/2005 | Laghi |
| 2004/0059433 | A1 | | 3/2004 | Slemker et al. |

FOREIGN PATENT DOCUMENTS

| | | | |
|---|---|---|---|
| GB | 2357725 A | | 7/2001 |
| JP | 3103785 | * | 6/2004 |

* cited by examiner

*Primary Examiner*—Bruce E. Snow
(74) *Attorney, Agent, or Firm*—Taft Stettinius & Hollister LLP

(57) ABSTRACT

A cosmesis includes a thigh component and a shin component that fit over a prosthetic knee joint. The thigh component and shin component are pivotally joined along an axis of rotation coinciding with that of the prosthetic knee joint. The thigh component and shin component can include internal contours molded into their inside walls to seat the prosthetic knee joint securely therein. The knee ball region of the thigh component can be made relatively thicker to provide a protective cushion and allow the patient to kneel. Additionally, a floating knee cap can be fit over the knee ball area. The upper end of the thigh component can be made of sufficiently thin material to permit rolling onto itself.

18 Claims, 7 Drawing Sheets

KNEE COSMESIS

BACKGROUND OF THE INVENTION

This invention relates to prosthetic devices, and specifically to a cosmesis for covering a prosthetic knee joint.

Prosthetic devices, such as prosthetic limbs, can be fitted with a cosmetic covering, sometimes called a cosmesis, that is designed to approximate the visual appearance of a human limb. One technique for fabricating such a cosmesis contemplates an encapsulation of the endoskeletal components of the prosthetic limb with a matrix substance (i.e. rigid foam) formed from a liquid resin containing a blowing agent which by/through application and control of appropriate conditions creates a foamed-in-place matrix, mass, or body, which is thereafter processed (i.e. milled and/or ground) by appropriate tooling and finishing to approximate the appearance/contour of the limb replaced. In a variant approach, a form or enclosure is positioned about the endoskeletal components as to define a cavity; and thence, there is introduced thereto, a volume of liquid resin containing a suitable blowing agent. Thereafter heat and/or pressure is applied to convert same to a cellular matrix which is hopefully of lower weight.

A cosmesis made in this manner has a drawback that the foam-in-place material must be usually destroyed if the endoskeletal components, which may include hydraulic units, control units, sockets, interconnection components, etc., require adjustment, replacement, and/or service in any respect.

Accordingly, there is a need for a cosmesis that is easier to implement and is applied in such a way that permits access to the internal prosthetic device components without need for destructive removal. The present invention addresses this need as well as many other needs as will be apparent to persons of ordinary skill in the art.

SUMMARY

The present invention provides a cosmesis including a thigh component and a shin component that fit over a prosthetic knee joint. The thigh component and shin component are pivotally joined along an axis of rotation coinciding with that of the prosthetic knee joint.

Accordingly, it is a first aspect of the present invention to provide a cosmesis for use with a prosthetic knee including: a substantially tubular thigh component made of a rubber-like material and having an upper end and a lower end, the upper end resembling at least a lower portion of a human thigh, the lower end comprising a knee-ball section adapted to receive a proximal segment of an endoskeletal knee chassis; and a substantially tubular shin component made of a rubber-like material and having an upper end and a lower end, the upper end adapted to receive a distal segment of the endoskeletal knee chassis; where the thigh component and the shin component are adapted to be pivotally joined along an axis of rotation that coincides with the axis of rotation of the endoskeletal knee chassis. In detailed embodiments, the thigh component and shin component can be adapted to hold the proximal or distal segment of the endoskeletal knee chassis securely therein, which can be accomplished using internal contours, molded integrally within the thigh or shin component, having a shape that is adapted to fit securely against at least a portion of the surface of the proximal or distal segment of the endoskeletal knee chassis.

In an alternative detailed embodiment of the first aspect of the present invention, the knee-ball section of the thigh component is relatively thicker than the upper end of the thigh component and includes a rounded bottom end. In another alternative detailed embodiment, the thigh component and the shin component are made of flexible urethane. In another alternative detailed embodiment, the thigh component is adapted to be joined to, and removed from, the proximal segment of the endoskeletal knee chassis manually by a user; and the shin component is adapted to be joined to, and removed from, the distal segment of the endoskeletal knee chassis manually by a user. In another alternative detailed embodiment, the upper end of the thigh component is adapted to be rolled onto itself such that the upper end can be rolled down approximate the location where it joins the lower end, and can be thereafter rolled up about a proximal prosthetic limb component and/or patient's residual limb.

In another alternative detailed embodiment of the first aspect of the present invention, the cosmesis further includes: a floating knee cap component; a first attachment section, a first end of which is joined to the floating knee cap component and a second end of which is joined to the shin component at a fixed point; and a second attachment section, a first end of which is joined to the floating knee cap component and a second end of which is joined to the thigh component at a variable point; where the thigh component can rotate with respect to the shin component. In a more detailed embodiment, the variable point includes a slider joined to the second attachment section, the slider being adapted to slide longitudinally along a slot in the thigh component. In an another more detailed embodiment, the floating knee cap component is made of flexible urethane.

It is a second aspect of the present invention to provide a prosthetic knee joint including: an endoskeletal knee chassis having a proximal segment and a distal segment, the proximal and distal segments being pivotally joined along an axis of rotation; a substantially tubular thigh cosmesis component having an upper end and a lower end, the lower end comprising a knee-ball section seating the proximal segment of the endoskeletal knee chassis; and a substantially tubular shin cosmesis component seating the distal segment of the endoskeletal knee chassis; where the thigh cosmesis component and the shin cosmesis component are pivotally joined along an axis of rotation that coincides with the axis of rotation of the endoskeletal knee chassis. In detailed embodiments, the shin cosmesis component and the thigh cosmesis component are formed from a semi-rigid material, which can be flexible urethane. The semi-rigid material can be colored as a skin-tone color. Additionally, the second aspect of the present invention may be practiced with any of the features or embodiments, or any combination thereof, described above with reference to the first aspect.

These and other aspects and embodiments will be apparent from the following description, the accompanying drawings, and the appended claims.

DETAILED DESCRIPTION

The exemplary embodiments of present invention provide a cosmesis for a prosthetic knee joint. In an exemplary embodiment, the prosthetic knee joint has the form described in co-pending U.S. Patent Application Publication Number 2004/0059433, the disclosure of which is incorporated herein by reference. But it will be apparent to persons of ordinary skill in the art that other types of prosthetic knee joints can be used as well.

Figure 1:
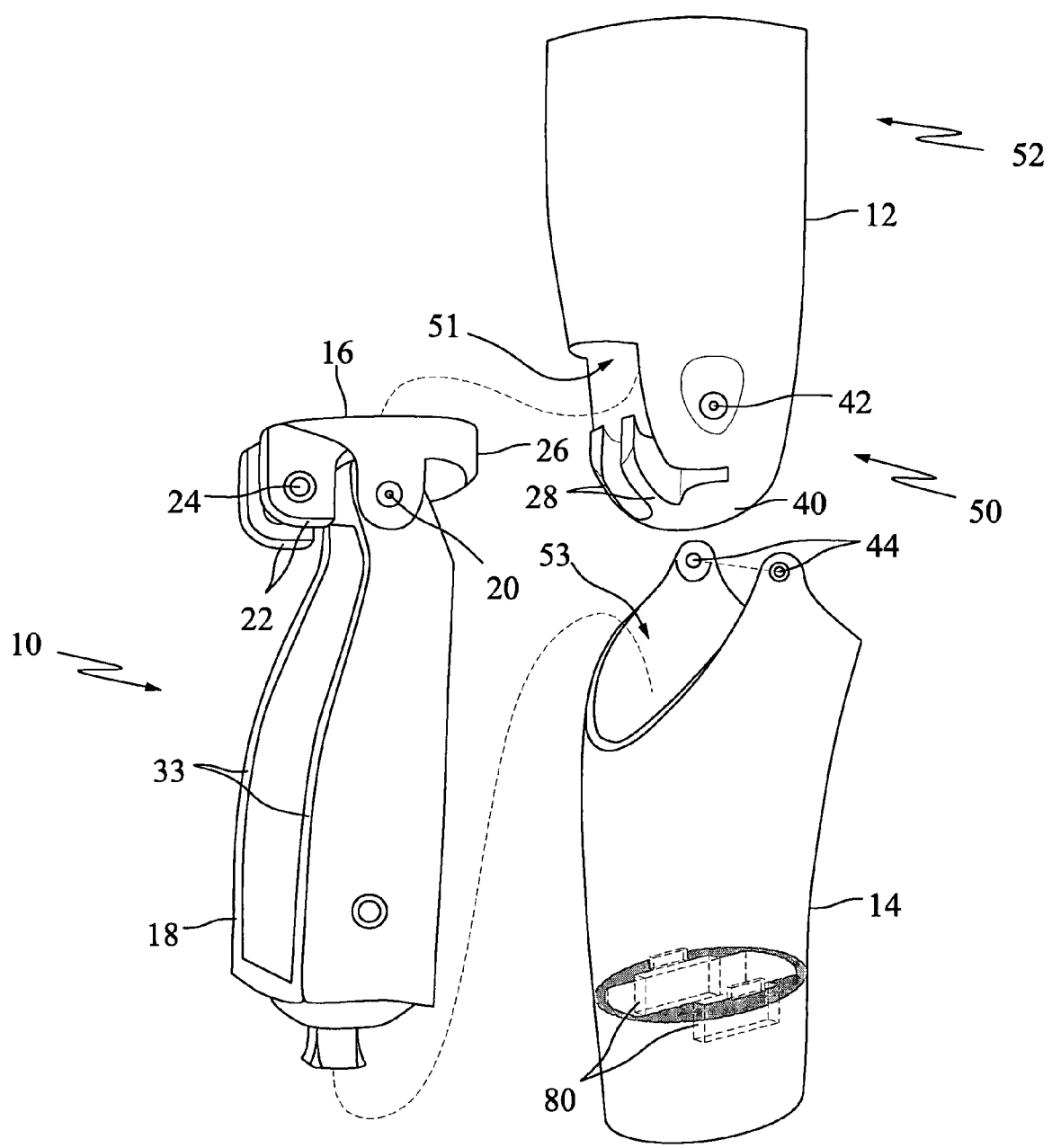
FIG. 1 is an exploded view showing the prosthetic knee joint 10 and a two-part cosmesis, according to an exemplary embodiment of the present invention.

FIG. 1 is an exploded view showing the prosthetic knee joint 10 and a two-part cosmesis, according to an exemplary embodiment of the present invention. The cosmesis generally includes a tubular or conical thigh component 12 and a tubular shin component 14. The knee joint 10 (also called an endoskeletal knee chassis) includes a proximal segment 16 and a distal segment 18. The proximal segment 16 is pivotally coupled to the distal segment 18 by a hinge assembly 20. The proximal segment 16 includes posterior projections 22 having holes 24 extending therethrough by which a hydraulic or pneumatic piston assembly (not shown) for operating the knee joint may be coupled. The cosmesis's thigh component 12 has lateral side holes 42, and the cosmesis's shin component 14 has complementary lateral side holes 44, which will be used to join the thigh component 12 and the shin component 14 together by a hinge such that they can rotate about the axis defined by the holes.

In an exemplary embodiment, the thigh component 12 and the shin component 14 of the cosmesis are made of a semi-rigid material such as flexible urethane, but the cosmesis can be made of other suitable materials known to persons skilled in the art, such as flexible silicone. The materials can be colored or painted, for example, in various skin tone colors to resemble the patient's skin tone. The thigh component 12 generally includes a relatively thinner and more resilient proximal thigh region 52 and a relatively thicker and more rigid distal knee ball region 50. The relatively hard and somewhat semispherical knee ball region 50 can be made of thicker rubber to allow for seating of the knee joint 10 therein, and to provide a cushioned weight-bearing surface for the knee, as explained below.

Figure 4:
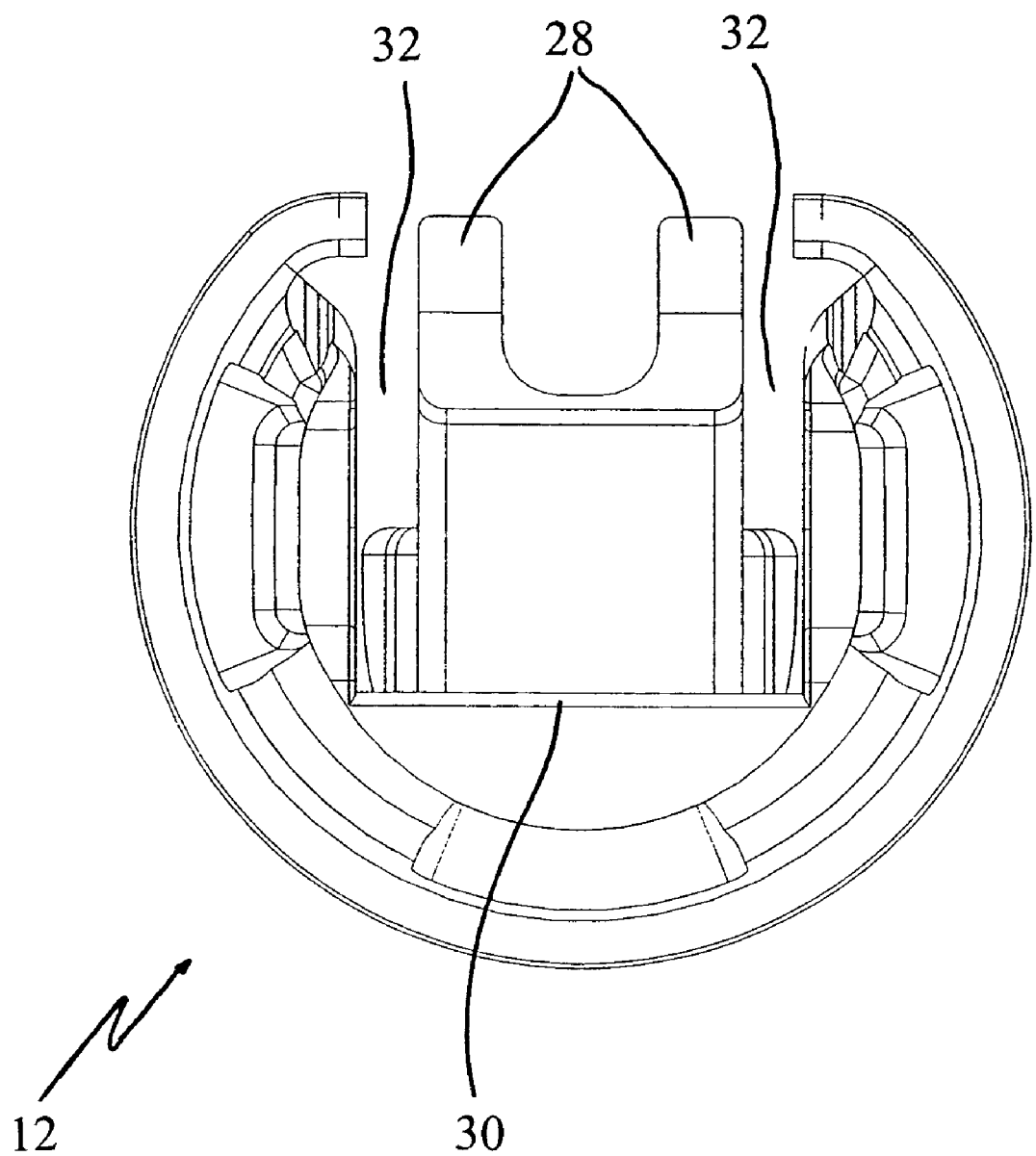
FIG. 4 shows a top plan view of the thigh component of the cosmesis, according to an exemplary embodiment of the present invention.

Referring to FIG. 1, the proximal segment 16 of the knee joint 10 is received through a distal posterior opening 51 in the cosmesis's thigh component 12, while the distal segment 18 of the knee joint 10 is received through a proximal opening 53 in the cosmesis's shin component 14. The inside surfaces of the cosmesis can be molded to provide seats for the components of the knee joint 10 when it is inserted into the cosmesis. For example, the two tooth-like protrusions 28 near the bottom of the thigh component 12 and extending into the opening 51 provide a seat on which the posterior projections 22 of the proximal segment 16 of the knee joint 10 will rest when inserted into the thigh component 12. A shelf-like seat 30 is molded into the opposite (front side) wall of the thigh component 12, and the front face 26 of the proximal segment 16 will be seated against this seat 30. FIG. 4, which is a top plan view of the thigh component 12, shows these molded protrusions 28 and shelf-like seat 30 more clearly. Two grooves 32 in the bottom of the thigh component 12 allow the parallel longitudinal shin bars 33 of the distal segment 18 of the knee joint 10 to extend downward from the thigh component 12.

In addition to seating the proximal segment 16 inside the cosmesis's thigh component 12, this design allows the knee joint 10 to be easily inserted into and removed from the cosmesis. In the exemplary embodiment, by rotating the knee joint approximately 90 degrees, the front face 26 of the proximal segment 16 can be inserted through the opening 51 into the cosmesis's thigh component 12 such that it passes above the tooth-like protrusions 28. Meanwhile, the bars 33 of the knee joint's distal segment 18 slide into the grooves 32 in the bottom of the cosmesis's thigh component 12, with the tooth-like protrusions 28 passing between the bars 33 of the distal segment 18. Once the proximal segment 16 has been seated within the cosmesis's thigh component 12, with its posterior projections 22 seated snugly against the tooth-like protrusions 28 and its front face 26 snugly seated against the seat 30, the knee joint can be rotated into its extended position so the distal segment 18 extends downward.

In the exemplary embodiment, the shin component 14 of the cosmesis also has shelf-like seats 80 molded into opposing sides to provide a seat to hold the bottom end 19 of the distal segment 18 in place when the cosmesis's shin component 14 is inserted over the distal segment 18 of the knee joint 10.

Figure 2:
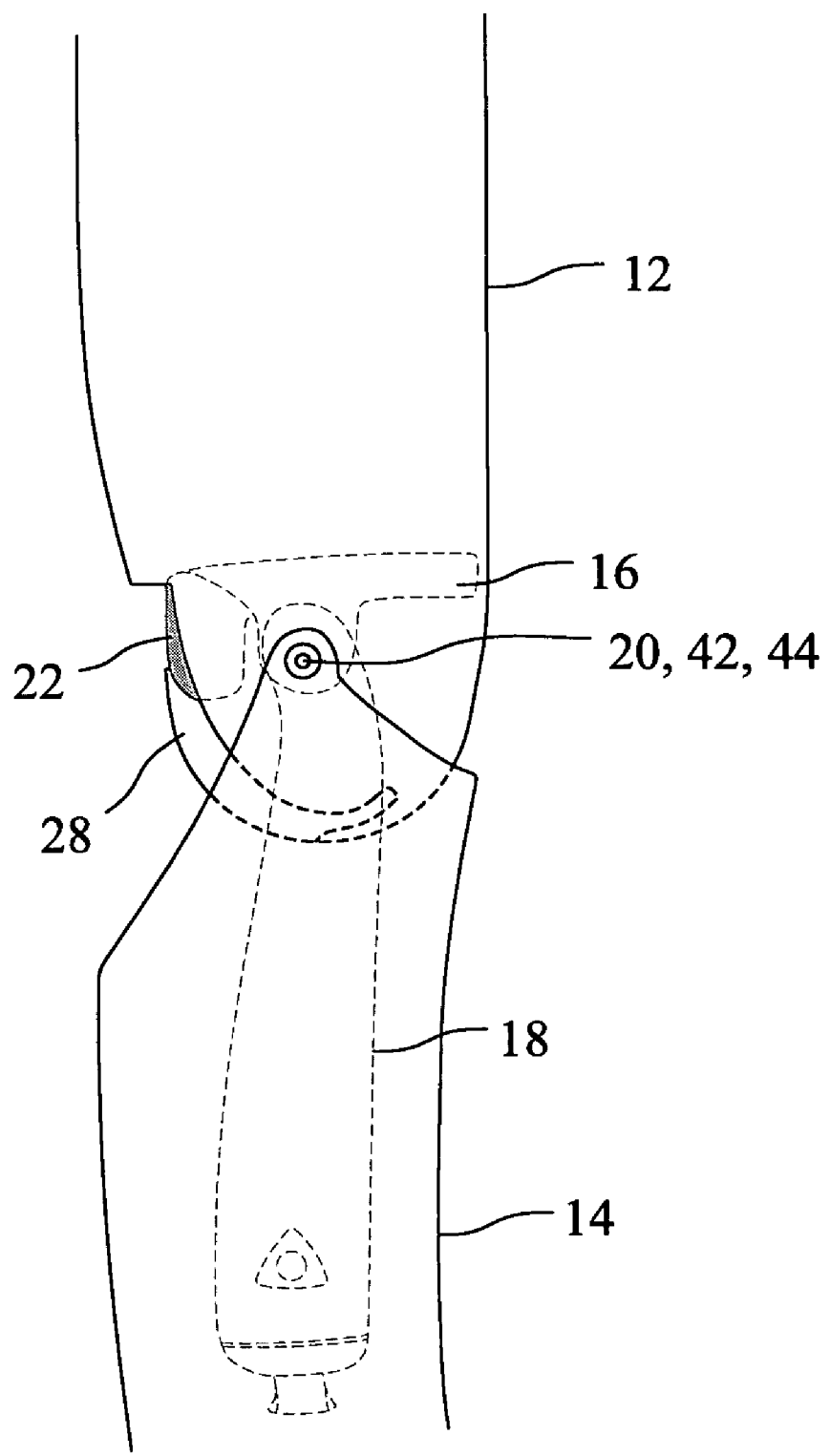
FIG. 2 shows the knee joint inserted into the cosmesis, according to an exemplary embodiment of the present invention.

FIG. 2 shows the knee joint 10 inserted into the thigh component 12 and the shin component 14 of the cosmesis. The proximal segment 16 of the knee joint 10 is seated in the molded seating areas in the cosmesis's thigh component 12, and the distal segment 18 of the knee joint 10 is seated in the molded seating areas in the cosmesis's shin component 14, as explained above. This ensures that the cosmesis's thigh component 12 remains secured relative to the proximal segment 16 and the cosmesis's shin component 14 remains secured relative to the distal segment 18. The thigh component 12 and shin component 14 are pivotally joined using a bolt or other axial hinge member to join each of the thigh component's holes 42 with one of the shin component's holes 44. The axis defined by the holes 42 and 44 and the axial members used to join them coincides with the axis defined by the hinge 20 of the knee joint 10. This common axis of rotation allows the cosmesis's thigh component 12 and shin component 14 to remain joined and to remain secured to the knee joint 10 as the knee joint rotates about its hinge 20.

Figure 3:
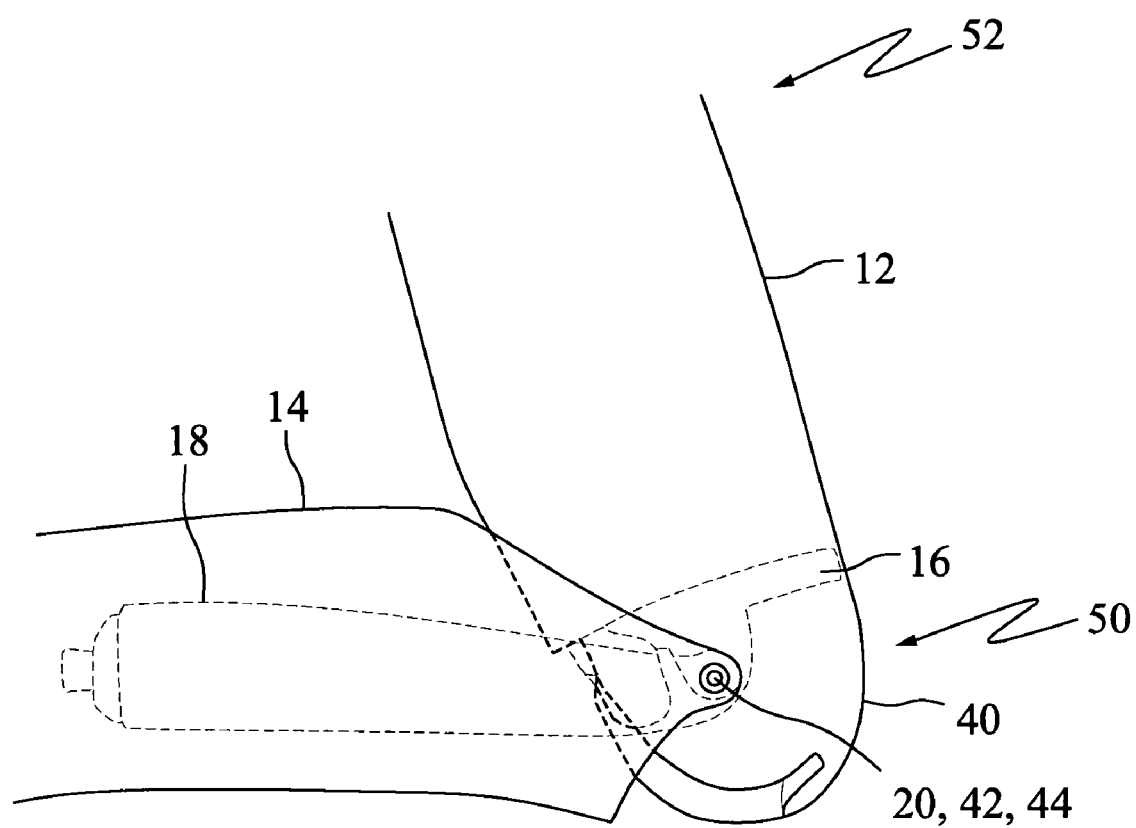
FIG. 3 shows the knee joint and cosmesis in a bent position, according to an exemplary embodiment of the present invention.

FIG. 3 shows the knee joint in a bent position as would allow the patient to kneel. The entire assembly has rotated about the axis defined by the hinge 20 of the knee joint 10 and the holes 42 and 44 of the cosmesis. In this kneeling position, where the lower leg (as represented by the distal segment 18 of the knee joint 10 and the cosmesis's shin component 14) is approximately parallel to the ground, the patient's body weight is supported by the substantially hard and somewhat semispherical distal end dome 40 of the knee ball region 50. In the exemplary embodiment, this knee ball region 50 of the cosmesis's thigh component 12 is made to be thicker than the proximal thigh portion 52 of the thigh component 12 to provide more hardness and force-bearing capability. In the exemplary embodiment, the rubber-like material of the knee ball region 50 is solid from the top surfaces of the tooth-like projections 28 and seat 30 to the bottom end of the dome 40 (of course, with the exception of the channels 32 and other mounting expedients). This enables the patient to kneel using the prosthetic device, and the cosmesis provides a cushion for the knee joint 10 to allow it to more reliably bear the weight that the patient puts on it when kneeling.

As will be apparent to persons of ordinary skill in the art, this embodiment provides a relatively modular knee cosmesis for a prosthetic limb with relatively simple donning and doffing capabilities. Thus, if adjustments are necessary for the endoskeletal prosthetic limb components, the cosmesis can be easily removed and reapplied before and after such adjustments. Additionally, the use of a semi-rigid material allows the cosmesis to be pre-fabricated to generic specifications that will give it a size and shape suitable for a majority of patients, thereby permitting faster and more efficient fabrication, as compared to other cosmesis designs.

Figure 5:
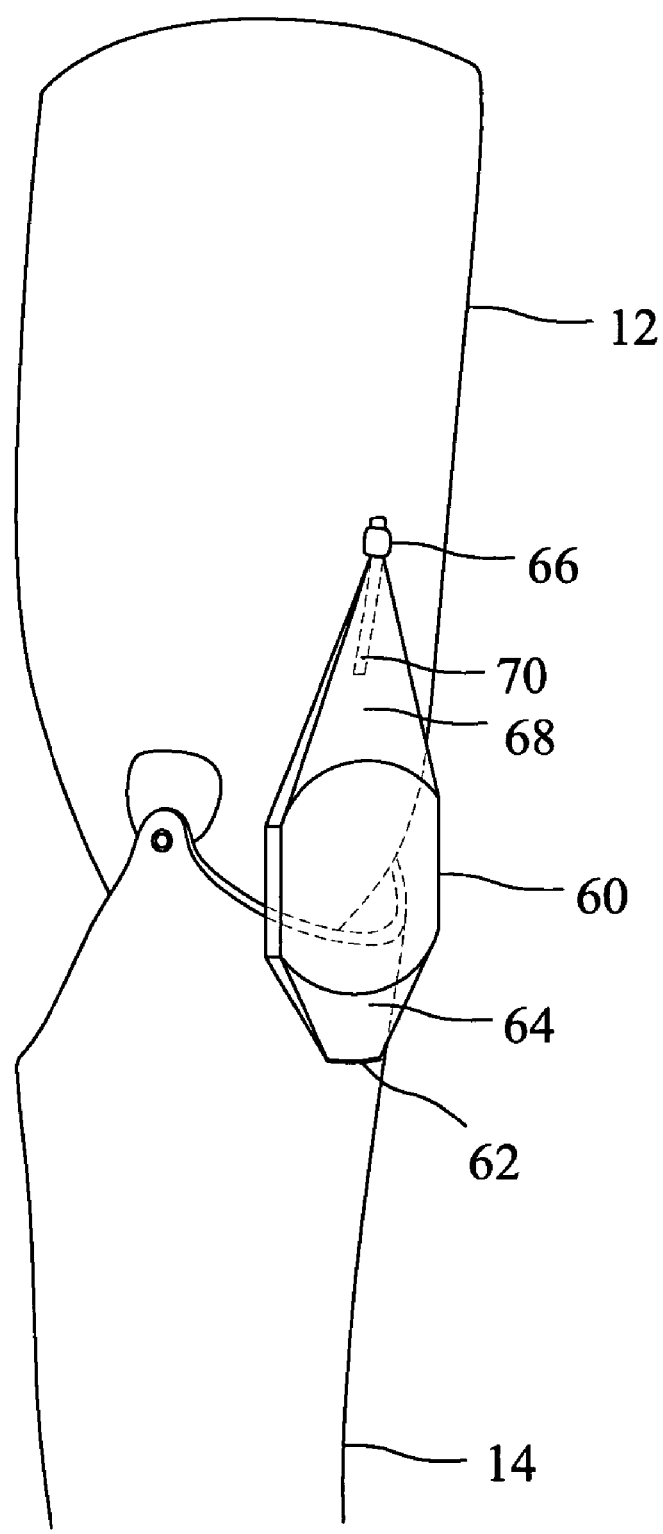
FIGS. 5 and 6 show the cosmesis with a floating knee cap, according to an exemplary embodiment of the present invention.
Figure 6:
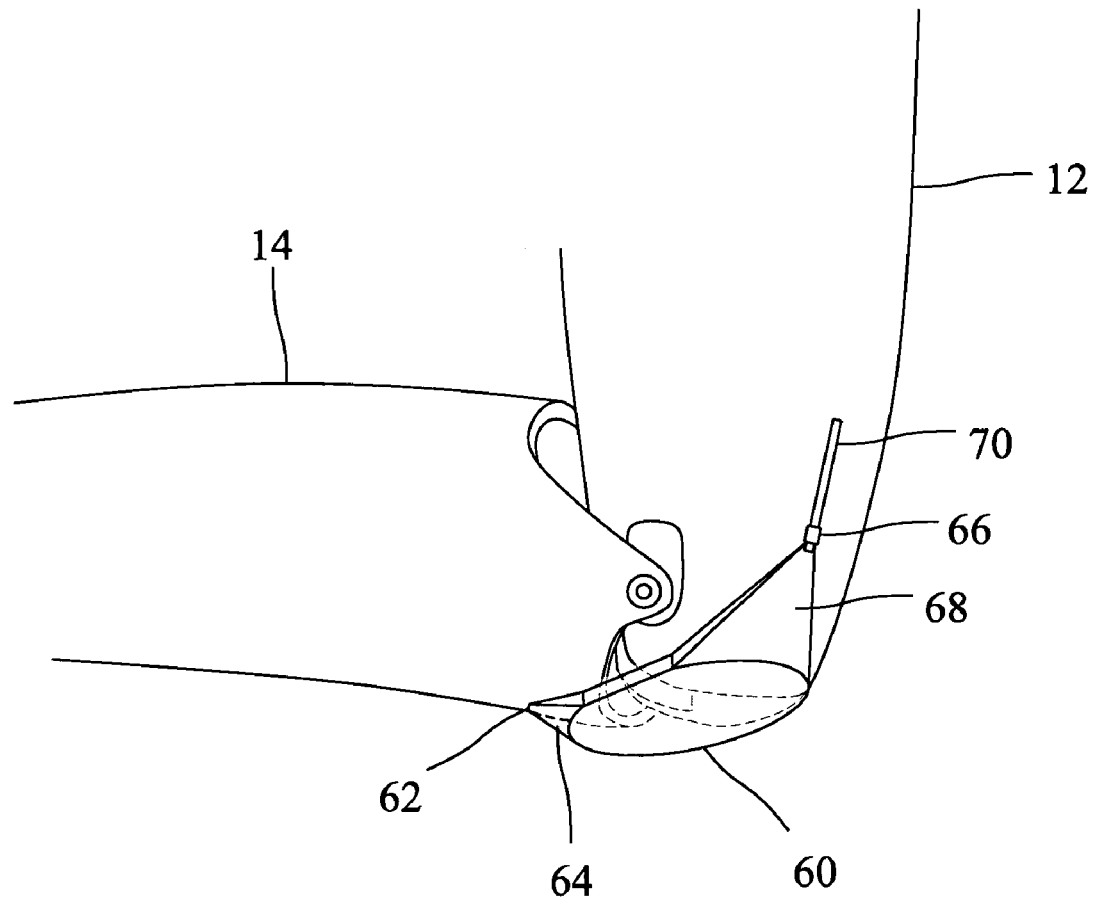

In an alternate exemplary embodiment, a relatively hard floating knee cap can be joined to the cosmesis at the knee, as shown in FIGS. 5 and 6. The knee cap 60 is joined by a first attachment section 64 to the cosmesis's shin component 14 at point 62. The attachment section 64 can be made of a semi-rigid material such as flexible urethane, and it can be molded integrally with the knee cap 60. Alternatively, the attachment section 64 can be made of other suitable materials known to persons skilled in the art, such as rubber or a fabric material such as nylon having elastic threads woven therein. The knee cap is joined by a second attachment section 68, which can be formed in the same manner as the first attachment section 64, to the cosmesis's thigh component 12 at point 66. The attachment point 66 can be implemented using a sliding piece that can slide along a track or slot 70 in the surface of the thigh component 12. This sliding capability of the upper attachment point 66 allows the knee cap 60 to "float" with respect to the thigh component 12 as the knee joint is bent, as seen in FIG. 6. FIG. 6 shows the knee in a bent or kneeling position, with the knee cap 60 in a substantially horizontal position adapted to bear the patient's weight in the kneeling position, as in a human knee. The slideable upper attachment point 66 is now located near the bottom end of the track 70 in the cosmesis's thigh component 12, resulting from the increased distance along the thigh component 12 when the knee joint is rotated. Alternatively, if the second attachment section 68 is made of rubber or other material capable of stretching, the upper attachment point 66 can be fixed relative to the cosmesis's thigh component 12.

Figure 7:
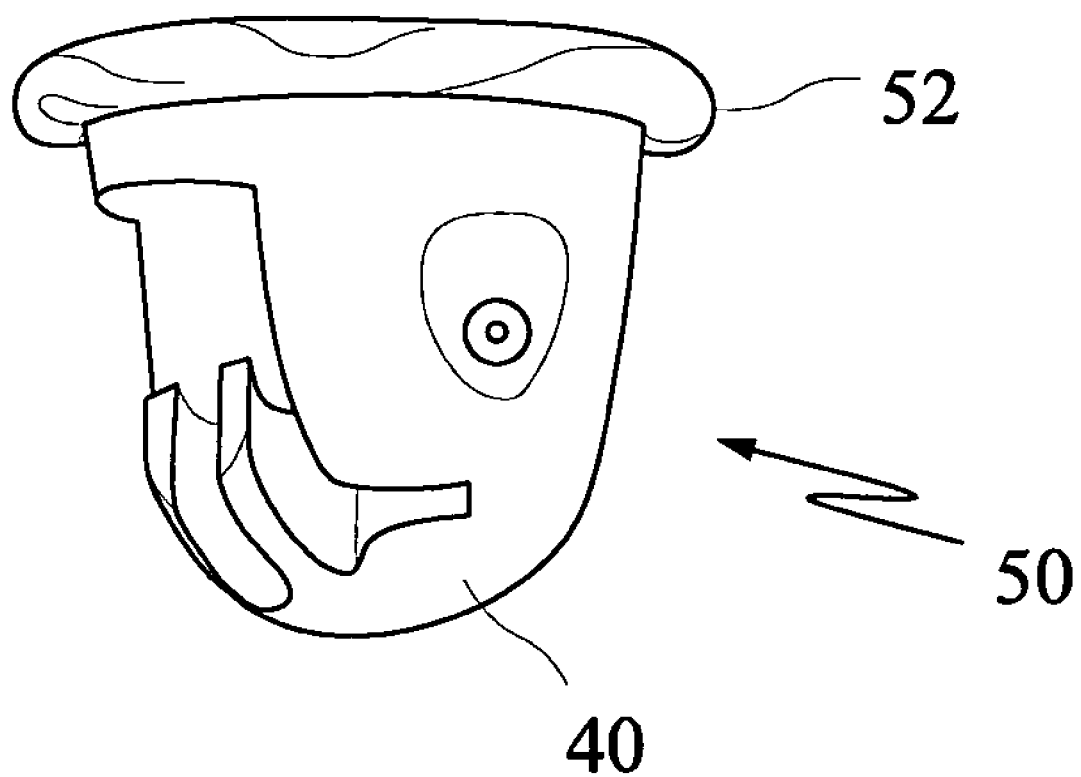
FIG. 7 shows the upper lateral surface of the thigh component rolled onto itself to allow easier application to a patient's residual limb, according to an exemplary embodiment of the present invention.

FIG. 7 shows an embodiment in which the cosmesis's thigh component 12 has a rollable sheath construction that allows for easier application to the patient's residual limb. The knee ball region 50 is made of a relatively thick rubber-like material and has a relatively hard consistency, as described above. The proximal thigh portion 52 can be made sufficiently thin that it can be rolled onto itself, as shown in FIG. 7. This configuration allows the patient's residual limb to be inserted into the thigh component 12 more easily. After the patient's residual limb has been inserted into the thigh component 12 and attached to the proximal segment 16 of the knee joint 18 residing therein, the proximal thigh portion 52 can be unrolled onto the patient's residual limb (or onto the hard outer socket of the prosthetic limb into which the residual limb is received).

Having described the invention with reference to embodiments, it is to be understood that the invention is defined by the claims, and it is not intended that any limitations or elements describing the embodiments set forth herein are to be incorporated into the meanings of the claims unless such limitations or elements are explicitly listed in the claims. Likewise, it is to be understood that it is not necessary to meet any or all of the identified advantages or objects of the invention disclosed herein in order to fall within the scope of any claims, since the invention is defined by the claims and since inherent and/or unforeseen advantages of the present invention may exist even though they may not have been explicitly discussed herein.

What is claimed is:

1. A prosthetic knee joint, comprising:
an endoskeletal knee chassis having a proximal segment and a distal segment, the proximal and distal segments being pivotally joined along an axis of rotation, the proximal segment including at least one posterior projection;
a substantially tubular thigh cosmesis component having an upper end and a lower end, the lower end comprising a knee-ball section seating the proximal segment of the endoskeletal knee chassis; and
a substantially tubular shin cosmesis component seating the distal segment of the endoskeletal knee chassis;
wherein the thigh cosmesis component and the shin cosmesis component are pivotally joined along an axis of rotation that coincides with the axis of rotation of the endoskeletal knee chassis; and
wherein the thigh cosmesis component includes a distal posterior opening that receives the proximal segment of the endoskeletal knee and includes at least one protrusion extending posteriorly into the distal posterior opening, the protrusion providing a seat for the at least one posterior projection of the proximal segment.

2. The prosthetic knee joint of claim 1, wherein
the shin cosmesis component and the thigh cosmesis component are formed from a semi-rigid material.

3. The prosthetic knee joint of claim 2, wherein
the knee-ball section of the thigh cosmesis component is relatively thicker than the upper end of the thigh cosmesis component.

4. The prosthetic knee joint of claim 1, wherein
the upper end of the thigh cosmesis component is adapted to be rolled onto itself such that the upper end can be rolled down approximate the location where it joins the lower end.

5. The prosthetic knee joint of claim 1, wherein
the lower end of the thigh cosmesis component is adapted to hold the proximal segment of the endoskeletal knee chassis securely therein, thereby securing the proximal segment from moving relative to the thigh cosmesis component.

6. The prosthetic knee joint of claim 5, wherein
the lower end of the thigh cosmesis component includes internal contours, molded integrally therein, having a shape that is adapted to fit securely against at least a portion of the surface of the proximal segment of the endoskeletal knee chassis.

7. The prosthetic knee joint of claim 1, wherein
the shin cosmesis component is adapted to hold the distal segment of the endoskeletal knee chassis securely therein, thereby securing the distal segment from moving relative to the shin cosmesis component.

8. The prosthetic knee joint of claim 7, wherein
the shin cosmesis component includes internal contours, molded integrally therein, having a shape that is adapted to fit securely against at least a portion of the surface of the distal segment of the endoskeletal knee chassis.

9. The prosthetic knee joint of claim 1, wherein
the distal segment of the endoskeletal knee chassis includes a pair of parallel, vertically extending shin bars extending from substantially approximate the axis of rotation down into the shin cosmesis component; and the lower end of the thigh cosmesis component includes a pair of grooves extending from the posterior receiving the shin bars therein;

wherein the shin bars may move in a posterior direction within the grooves when the endoskeletal knee chassis pivots from a knee-unbent orientation to a knee-bent orientation.

10. The prosthetic knee joint of claim 9, wherein the proximal segment of the endoskeletal knee includes a parallel pair of the posterior projections; and the thigh cosmesis component includes a parallel pair of the posterior extending protrusions, respectively seating the posterior projections.

11. The prosthetic knee joint of claim 10, wherein the pair of grooves at the lower end of the thigh cosmesis component flank the pair of posterior extending protrusions.

12. The prosthetic knee joint of claim 1, wherein the axis of rotation is located proximally with respect to the knee ball section of the thigh cosmesis component.

13. A cosmesis for use with a prosthetic knee, comprising:

a substantially tubular thigh component made of a rubber-like material and having an upper end and a lower end, the upper end resembling at least a lower portion of a human thigh, the lower end comprising a knee-ball section adapted to receive a proximal segment of an endoskeletal knee chassis; and a substantially tubular shin component made of a rubber-like material and having an upper end and a lower end, the upper end adapted to receive a distal segment of the endoskeletal knee chassis;

wherein the thigh component and the shin component are are pivotally joined along an axis of rotation that coincides with the axis of rotation of the endoskeletal knee chassis;

wherein the axis of rotation is located proximally from a distal end of the knee-ball section of the thigh component;

wherein at least one of the thigh component and the shin component includes at least one hole located along the axis of rotation, the hole receiving an axial member extending between the thigh component and the shin component; and wherein the upper end of the thigh component is adapted to be rolled onto itself such that the upper end can be rolled down approximate the location where it joins the lower end, and can be thereafter rolled up about a proximal prosthetic limb component and/or patients residual limb.

14. A cosmesis for use with a prosthetic knee, comprising:

a substantially tubular thigh component made of a rubber-like material and having an upper end and a lower end, the upper end resembling at least a lower portion of a human thigh, the lower end comprising a knee-ball section adapted to receive a proximal segment of an endoskeletal knee chassis;

a substantially tubular shin component made of a rubber-like material and having an upper end and a lower end, the upper end adapted to receive a distal segment of the endoskeletal knee chassis;

a floating knee cap component;

a first attachment section, a first end of which is joined to the floating knee cap component and a second end of which is joined to the shin component at a fixed point; and a second attachment section, a first end of which is joined to the floating knee cap component and a second end of which is joined to the thigh component at a variable point;

wherein the thigh component and the shin component are adapted to be pivotally joined along an axis of rotation that coincides with the axis of rotation of the endoskeletal knee chassis; and wherein the thigh component can rotate with respect to the shin component.

15. The cosmesis of claim 14, wherein the variable point includes a slider joined to the second attachment section, the slider being adapted to slide longitudinally along a slot in the thigh component.

16. The cosmesis of claim 14, wherein the floating knee cap component is made of flexible urethane.

17. A prosthetic knee joint, comprising:

an endoskeletal knee chassis having a proximal segment and a distal segment, the proximal and distal segments being pivotally joined along an axis of rotation;

a substantially tubular thigh cosmesis component having an upper end and a lower end, the lower end comprising a knee-ball section seating the proximal segment of the endoskeletal knee chassis;

a substantially tubular shin cosmesis component seating the distal segment of the endoskeletal knee chassis;

a floating knee cap component coupled between the thigh cosmesis component and the shin cosmesis component;

a first attachment section, a first end of which is joined to the floating knee cap component and a second end of which is joined to the shin cosmesis component at a fixed point; and a second attachment section, a first end of which is joined to the floating knee cap component and a second end of which is joined to the thigh cosmesis component at a variable point;

wherein the thigh cosmesis component and the shin cosmesis component are pivotally joined along an axis of rotation that coincides with the axis of rotation of the endoskeletal knee chassis.

18. The prosthetic knee joint of claim 17, wherein the variable point includes a slider joined to the second attachment section, the slider being adapted to slide longitudinally along a slot in the thigh cosmesis component.

* * * * *